United States Patent
Tullo et al.

(10) Patent No.: US 6,905,711 B1
(45) Date of Patent: Jun. 14, 2005

(54) ANTIMICROBIAL AGENTS, PRODUCTS INCORPORATING SAID AGENTS AND METHODS OF MAKING PRODUCTS INCORPORATING ANTIMICROBIAL AGENTS

(75) Inventors: Louis J. Tullo, Hewlett, NY (US); Leonard Pinchuk, Miami, FL (US)

(73) Assignee: Smart Anti-Microbial Solutions, LLC, Stamford, CT (US)

( * ) Notice: Subject to any disclaimer, the term of this patent is extended or adjusted under 35 U.S.C. 154(b) by 23 days.

(21) Appl. No.: 10/138,160

(22) Filed: May 2, 2002

(51) Int. Cl.$^7$ .................. A01N 59/16; A01N 59/20
(52) U.S. Cl. ............... 424/618; 424/78.37; 424/617; 424/630; 424/641; 424/646; 424/649; 424/650; 424/651; 424/653; 424/405; 523/122
(58) Field of Search ............ 424/405, 404, 424/400, 409, 421, 78.1, 78.26, 78.27, 78.35, 78.37, 618, 617; 523/122

(56) References Cited

U.S. PATENT DOCUMENTS

| | | | |
|---|---|---|---|
| 3,864,468 A | 2/1975 | Hyman et al. | 424/16 |
| 4,205,043 A | 5/1980 | Esch et al. | 422/56 |
| 4,282,366 A | 8/1981 | Eudy | 556/413 |
| 4,343,853 A | 8/1982 | Morrison | 428/233 |
| 4,411,928 A | 10/1983 | Baldwin | 427/2 |
| 4,421,719 A | 12/1983 | Burleigh | 422/57 |
| 4,472,353 A | 9/1984 | Moore | 422/58 |
| 4,533,435 A | 8/1985 | Intili | 162/161 |
| 4,772,560 A | 9/1988 | Attar | 436/165 |
| 4,866,192 A | 9/1989 | Plueddemann et al. | 556/410 |
| 4,933,178 A * | 6/1990 | Capelli | 424/78 |
| 5,026,723 A | 6/1991 | Katayama et al. | 514/441 |
| 5,035,860 A | 7/1991 | Kleingeld et al. | 422/61 |
| 5,064,613 A | 11/1991 | Higgs et al. | 422/16 |
| 5,171,536 A | 12/1992 | Evers | 422/88 |
| 5,709,870 A | 1/1998 | Yoshimura et al. | 424/404 |
| 5,869,172 A | 2/1999 | Caldwell | 428/306 |
| 6,030,632 A * | 2/2000 | Sawan et al. | 424/405 |
| 6,120,784 A | 9/2000 | Snyder, Jr. | 424/404 |
| 6,121,012 A | 9/2000 | Falkowski et al. | 435/39 |
| 6,228,128 B1 | 5/2001 | Johansen et al. | 8/137 |
| 6,251,386 B1 | 6/2001 | Johansen | 424/94.4 |
| 6,284,198 B1 | 9/2001 | Kirollos et al. | 422/87 |
| 6,325,969 B1 | 12/2001 | Aamodt et al. | 422/29 |

FOREIGN PATENT DOCUMENTS

WO 01/43788 * 6/2001

OTHER PUBLICATIONS

"Anthrax scare aids new firm . . . " By James Rosen, *The Sacramento Bee*, Internet News Journal, Nov. 4, 2001.
"Consolidated Graphics Introduces Antimicrobial Agent for Printed Matter" from weekly summary of news by *Printing Impressions* magazine, Jan. 11, 2002.
"Slim chance of anthrax on money" By Ryan Alkessi, *The Daily Camera*, Internet News Journal, Oct. 27, 2001.

* cited by examiner

*Primary Examiner*—Neil S. Levy
(74) *Attorney, Agent, or Firm*—Gordon & Jacobson, PC

(57) ABSTRACT

An antimicrobial agent includes an oligodynamic metal ion in a hydrophilic polymer binder or carrier. According to a presently preferred embodiment, the metal ion is silver and the hydrophilic polymer is polyurethane. According to a method of the invention, the antimicrobial agent is dissolved in dimethyl acetamide DMA, applied to paper by squeegee or the like and dried in an oven to flash off the solvent. The antimicrobial agent can be applied to other products by spraying and/or dipping and then drying to flash off solvent. A method of rendering a polymeric medical device antimicrobial is also disclosed.

27 Claims, No Drawings

ANTIMICROBIAL AGENTS, PRODUCTS INCORPORATING SAID AGENTS AND METHODS OF MAKING PRODUCTS INCORPORATING ANTIMICROBIAL AGENTS

BACKGROUND OF THE INVENTION

1. Field of the Invention

The invention relates to antimicrobial agents, products incorporating such agents, and methods of making such products. More particularly, the invention relates to an antimicrobial agent suitable for impregnating and/or coating paper products and for coating certain medical devices.

2. State of the Art

In October 2001, several prominent Americans received letters containing the bacteria anthrax. Since then, the U.S. Postal Service has taken many steps to prevent the spread of deadly disease via the mails. Although all of the contaminated letters consisted of paper envelopes containing paper notes with anthrax powder, it has yet to be proposed that paper be manufactured with antimicrobial agents as a means for preventing the spread of disease via the mails.

A survey of the relevant art reveals that antimicrobial agents have previously been incorporated into various products for various reasons. For example, U.S. Pat. No. 3,864,468 to Hyman et al, issued Feb. 4, 1975, discloses non-porous polymeric articles having an active agent applied to the surface. The active agents include antibacterial and antifungal agents as well as insecticides, etc. The articles disclosed include polymeric films and fabrics as well as laminated products including polymeric films.

U.S. Pat. No. 4,282,366 to Eudy, issued Aug. 4, 1981, discloses organosilicon quaternary ammonium antimicrobial compounds which are allegedly suitable for impregnating cellulose fabrics to inhibit the growth of disease causing microorganisms. The single example illustrates the treatment of Whatman No. 1 filter paper. Mixed results were observed over a period of days with the best results from higher concentrations of the active agent.

U.S. Pat. No. 4,343,853 to Morrison, issued Aug. 10, 1982, discloses an antimicrobial treated fabric construction. The brief disclosure mentions a test involving a sweatshirt but no quantitative data is provided to measure the efficacy of the treated fabric construction.

U.S. Pat. No. 4,411,928 to Baldwin, issued Oct. 25, 1983, discloses a process for applying a microbiocidal finish to a fabric product such as a surgeon's gown, medical drape, isolation gown, instrument wraps, and the like. The disclosed microbiocidal agent is a silicone quaternary amine. The fabric produced is stated to have a bacteriocidal effectiveness of more than 95% in one hour. However, no experimental data is provided to substantiate the claim of effectiveness.

U.S. Pat. No. 4,533,435 to Intilli, issued Aug. 6, 1985, discloses an antimicrobial additive incorporated into the binding agent of a heavy-duty, kraft-type paper having the characteristics of substantial density, air impermeability, and improved printability. The antimicrobial additives disclosed consist of halogenated aromatic nitriles; a salt of imazalil sulphate; 3,5,3',4'-tetrachlorosalicylanilide; and dichlorophene. The paper is intended for packaging surgical instruments or other sterile materials. It is stated that the antimicrobial additive migrates from within the binding agent onto the paper fibers to substantially eliminate the growth of micro-organisms thereon. However, no experimental data is provided to substantiate the claim of effectiveness.

U.S. Pat. No. 4,866,192 to Plueddemann et al., issued Sep. 12, 1989, discloses organosilicon quaternary ammonium antimicrobial compounds, particularly ammonium chloride derivatives of multifunctional diamino quaternary salts, and salts containing a combination of amino, ester, and fluoroalkyl, functionality. The compounds are not stated to be particularly useful for any specific application, although treatment of rayon cloth and use in moist towelettes is mentioned. When tested on rayon, results were mixed with higher concentrations yielding better results.

U.S. Pat. No. 5,026,723 to Katayama et al., issued Jun. 25, 1991, discloses a microbicidal/microbistatic synergistic composition for industrial use comprising a specific nitro-bromopropane derivative and 4,5-dichloro-1,2-dithiol-3-one and an industrial method of killing or inhibiting the growth of microorganisms using the same compounds, which are useful of microbicidal/microbistatic treatment in various industrial media such as water used in making paper, industrial cooling water and the like.

U.S. Pat. No. 5,064,613 to Higgs et al., issued Nov. 12, 1991, discloses a method of treating surfaces in order to eliminate microbial growth by adding an antibacterially effective amount of an organosilicon quaternary ammonium silatrane compound to the surface in order to destroy bacteria and fungi. The compounds were tested on cotton and polyester yielding mixed results with higher concentrations performing better than lower concentrations.

U.S. Pat. No. 5,709,870 to Yoshimura et al., issued Jan. 20, 1998, discloses a silver-containing antimicrobial agent which is said to be excellent in affinity to fiber, antimicrobial property, antifungus property and stability to heat and light. It comprises carboxymethyl cellulose containing silver in the amount of 0.01 to 1% by weight and having the degree of substitution to carboxymethyl group of not less than 0.4. The carboxymethyl cellulose may be a crosslinked compound to make the antimicrobial agent water resistant. The antimicrobial agent is said to be well suited for application to paper, leather and porous material. According to the test results reported, the sterilization ratio of the compounds was at best 86% and in most cases less than 70%.

U.S. Pat. No. 5,869,172 to Caldwell, issued Feb. 9, 1999, discloses a variety of internally coated webs. The disclosure includes methods for the treatment of porous webs to controllably cause additives and/or modifiers to orient on and within: (a) a thin film of a polymer composition encapsulating the structural elements (i.e., the fibers or filaments) making up the web, leaving at least some of the interstitial spaces open; (b) an internal layer of a polymer composition between the upper and lower surfaces of the web; or (c) some combination of the foregoing. One of the many modifiers disclosed is iodine as a biocidal and antimicrobial agent. No data were provided regarding the effectiveness of this treatment.

U.S. Pat. No. 6,120,784 to Snyder, Jr., issued Sep. 19, 2000, discloses a method of imparting anti-pathogenic properties to a substrate material comprising: (a) preparing a coating composition containing an anti-pathogenic agent consisting essentially of PVP-I and N-9 in a ratio of from about 100:0 to about 0:100 of PVP-I to N-9, the coating composition further containing a pre-mix solution with which the anti-pathogenic agent is intimately mixed in a ratio of from about 6:4 to about 8:2 of agent to pre-mix on a dry basis, and having a percent solids content of from about 5% to about 35% solids; (b) feeding the anti-pathogenic coating composition into a coating machine; (c) loading substrate onto the coating machine; (d) operating the coating machine such that the coating composition comes into intimate contact with at least one surface of the substrate; and (e) drying the coated substrate material. Suitable substrates for use in conjunction with the anti-pathogenic formulation include paper, paper laminates, non-woven materials, non-woven laminates, and other similar substrates. The invention is primarily concerned with substrates targeted for use in medical-type applications, such as surgical gowns and drapes, examining table paper, hospital bed pads, hospital bed inserts and sheeting, surgical masks and other hospital or medical-type applications.

U.S. Pat. No. 6,228,128 to Johansen et al., issued May 8, 2001, discloses a method of antimicrobial treatment using a combination of a laccase enzyme and an enhancer capable of killing or inhibiting microorganisms, more specifically microorganisms present in laundry, on hard surfaces, on skin, teeth or mucous membranes; and for preserving food products, cosmetics, paints, coatings, etc., the composition comprising a laccase enzyme and an enhancing agent acting as an electron donor.

U.S. Pat. No. 6,251,386 to Johansen, issued Jun. 26, 2001, discloses an enzymatic composition capable of killing or inhibiting microbial cells or microorganisms, more specifically microbial cells or microorganisms present in laundry, on hard surfaces, in water systems, on skin, teeth or mucous membranes; and for preserving food products, cosmetics, paints, coatings, etc. The composition includes a haloperoxidase, a hydrogen peroxide source, a halide source, and an ammonium source, in particular an ammonium salt or an aminoalcohol, in which there is a hitherto unknown synergistic effect between the halide and the ammonium source.

U.S. Pat. No. 6,325,969 to Aamodt et al., issued Dec. 4, 2001, discloses a porous paper product impregnated with at least one chemical species. For example, paper impregnated with precursors of chlorine dioxide is disclosed. The chlorine dioxide suppresses the growth of bacteria. Other examples of antimicrobial agents include aqueous hydrogen peroxide, acetic acid, limonene in water, aqueous potassium sorbate and combinations thereof. These agents were tested by spraying them on paper. The tests measured the area in which growth of bacteria was prevented rather than the amount of bacteria killed.

All of the surveyed antimicrobial agents are intended to limit the growth of non-lethal bacteria and microorganisms such as mold and odoriferous growths which may be damaging but which are rarely life threatening. None of the known antimicrobial agents appears to be capable of killing anthrax bacteria on contact.

SUMMARY OF THE INVENTION

It is therefore an object of the invention to provide an antimicrobial agent which is capable of killing anthrax on contact.

It is also an object of the invention to provide an antimicrobial agent which is capable of killing anthrax on contact and which can be incorporated in paper products.

It is another object of the invention to provide methods of incorporating an antimicrobial agent, which is capable of killing anthrax on contact, with other products including paper products and certain medical products.

In accord with these objects which will be discussed in detail below, the antimicrobial agent of the present invention includes a metal ion in a hydrophilic polymer binder or carrier. According to a presently preferred embodiment, the metal ion is silver and the hydrophilic polymer is polyurethane. According to a method of the invention, the antimicrobial agent is dissolved in dimethyl acetamide DMA, applied to paper by spraying, squeegee the like and dried in an oven to flash off the solvent. The antimicrobial agent can be applied to other products by spraying and/or dipping and then drying to flash off solvent.

Paper coated with the antimicrobial agent of the invention was tested by NAMSA (Atlanta, Ga.) for antimicrobial activity using the Dow 923 "Shake-flask" test. After one hour 99.94% (the upper limit of the test equipment) of all bacteria were killed.

Additional objects and advantages of the invention will become apparent to those skilled in the art upon reference to the detailed description.

DETAILED DESCRIPTION OF THE PREFERRED EMBODIMENTS

In order for a paper treated with an antimicrobial agent to be effective in preventing the transmission of anthrax, the antimicrobial agent should be stable and remain potent over a relatively long time. It must be non-toxic to humans, is preferably non-coloring, inexpensive, and easy to apply to paper.

The antimicrobial agents according to the invention utilize a metal ion in conjunction with a hydrophilic polymer. The metallic ions, such as Ag, Au, Pt, Pd, Ir (i.e., the noble metals), Cu Sn, Sb, Bi and Zn, as well as many heavy metals are effective antimicrobials.

Metallic antimicrobials function by releasing metal ions into the microbe. The released ions react with protein and other anions (negative charged species) in the microbe and render the protein insoluble and thereby inactive. Inactive protein perturbs cellular function, disrupts membranes and prevents the normal activity and reproduction of DNA thereby essentially killing the microorganism. In order for antimicrobials to release metal ions into the microbe, the microbe must be in fluidic contact with the metal ion, i.e., they must both be in the same water medium. In addition, the metal ion must release from the substrate it is attached to, diffuse out to the microbe, penetrate the membrane of the microbe, seek protein, bind to it and then precipitate it. Importantly, most of the more deadly microbes, such as anthrax are not water-containing. The anthrax spore is essentially dry and inert to environmental conditions due to its durable membrane and lack of moisture within the membrane.

Of the metal ions mentioned above, silver ion (Ag+) is perhaps the best known metal ion antimicrobial due to its unusually good bioactivity at low concentrations. This bioactivity of silver is known as oligodynamic action. However, Ag+ is not stable. In the presence of light, Ag+ converts to Ag metal. This instability is a benefit for the photography industry. Ag+ is clear, Ag metal is opaque-black. For these reasons, Ag+ is not a likely candidate for an antimicrobial treatment of paper. Paper treated with Ag+ will turn black when exposed to light and will no longer have any antimicrobial effect. Even if the paper were not exposed to light, if Ag+ is released from the paper too rapidly, the Ag+ reservoir will be depleted, excess Ag+ will convert to its metal form and the antimicrobial activity will be compromised. If the Ag+ is released too slowly, however, it may not be present in sufficient quantity to be effective.

Despite the disadvantages of Ag+, the present invention has found a way to overcome these disadvantages and the disadvantage of metal ions in general (that they need water to work as antimicrobials) particularly with regard to very dry microbes such as anthrax spores.

According to the invention Ag+ is bound to a substrate which releases it at just the correct rate, protects it from light, and also hydrates easily with water, or more preferably remains wet for a long time. The substrate preferably contains wetting groups that are more than simple water absorbing groups; rather these groups essentially suck in water and bind the water to the surface somewhat permanently.

The substrate of the invention is easily rendered into a lacquer which can be applied to paper without mottling, softening, wetting, or the like. In addition, the solvents used to form the lacquer are preferably non-toxic, non-flammable, non-carcinogenic, non-mutagenic, etc.

An antimicrobial according to the invention therefore preferably includes a polymer or molecular substance that has pendant hydrophilic groups that include, sulfates, carboxylic acids, amines, hydroxyls, nitrates, phosphates, or in general, any functional group soluble in water. More preferably, the hydrophilic group is also capable of binding with an oligodynamic metal ion, such as Ag+ or Zn+. Negatively charged hydrophilic groups such as sulfates, phosphates, nitrates, carboxylates and the like, are therefore preferred.

Polymers useful for the solids content of the lacquer include polyurethane, polyamines, cellulose, cellulose acetate, triacetate, polyester, hydrogels, polyolefins, and any other polymer capable of dissolving or dispersing in a solvent. Chemical substances can include surfactants, silane coupling agents, etc., that have tails that are hydrophobic and head groups that are hydrophilic; the hydrophilic heads include the pendants mentioned above. Included in this list are the aforementioned polymers and chemical substances that have been further modified to increase solubility, increase their reactivity towards metal ions and modified further to modulate their activity in regard to the sustained release of the metal ions.

The antimicrobial agent of the invention is illustrated in five examples.

EXAMPLE 1

A polymer solution is made by dissolving 10 g of an aromatic polyether urethane such as Dow Chemical's Pellethane® 2363 75D in 18 g dimethyl acetamide (DMA) and 72 g tetrahydrofuran (THF) at 70° C. with mixing for. 3 hours.

The polyurethane is sulfonated and rendered hydrophilic by adding 21 ml of acetic anhydride and 12.5 ml of concentrated sulfuric acid to the polyurethane solution while it is being vigorously mixed. After the exothermic reaction subsides, the hydrophilic urethane is poured into a blender filled with water where the polyurethane is precipitated and chopped into small particles under agitation. The particulate slurry is poured through a wire sieve to remove the particles and rinsed repeatedly with water until the pH of the solution is between 4 and 8. The precipitated sulfonated polyurethane is then dried for 3 hours in an oven at 70° C.

The dried sulfonated polyurethane (10 g) is then redissolved in DMA. Films cast from this solution dry to clear and turn white opaque upon soaking in water for a few minutes. The opaque white transition is typical of polymers that absorb water thereby confirming that the polyurethane thus formed is hydrophilic.

The sulfonated polyurethane (10 g dissolved in 90 g DMA) solution is then reacted with silver nitrate by adding 0.2 g (2% by weight of polymer) of silver nitrate to the sulfonated polyurethane solution. The solution turns milky white after the addition thereby indicating a reaction between the sulfate groups and the silver nitrate.

The polyurethane with the silver sulfate groups is then squeegeed onto paper or the like and dried in an oven at 70° C. for 10 minutes to flash off the solvent. The dried coated paper is tested for elutable silver by placing a section of the coated paper under an ultraviolet lamp, adding a drop of water to a section of the paper and exposing the paper with the drop of water to the UV light for 15 to 20 minutes. It can easily be observed that the drop of water turns gray as the silver ion migrates from the substrate and is converted to silver metal by the ultraviolet light. Areas around the drop of water do not significantly change color.

Coated sections of paper produced according to this example were tested for antimicrobial activity by NAMSA using the Dow 923 "Shake-flask" test which involves shaking the sample in a flask with *staphylococcus aureus* bacteria for 1 hour and then for 24 hours and measuring the amount of bacteria killed. Results indicate that at one hour, 99.94%, or essentially all, of the bacteria were killed. The results at 24 hours were the same which suggests that there were no bacteria remaining to be killed, i.e. that 99.94% is the upper limit of the testing equipment.

The antimicrobial of this example provides a sustained release of Ag+ due to the sulfate counter-ions. The Ag+ is released at a rate sufficient to kill bacteria on contact but slow enough that the antimicrobial activity is maintained over a long time. The effective duration of the coating is dependent upon many factors, such as the thickness of the coating, the ratio of silver to polymer, and the degree of hydration of the system. The efficacy of typical coatings can last years depending upon the particular parameters.

EXAMPLE 2

A polymer solution is made by dissolving 10 g of an aromatic polyether urethane such as Dow Chemical's Pellethane® 2363 75D in 18 g dimethyl acetamide (DMA) and 72 g tetrahydrofuran (THF) at 70° C. with mixing for 3 hours. Silver sulfadiazine in the amount of 0.2 g is added to this solution and is mixed until well dispersed.

The polyurethane with the silver sulfadiazine is then squeegeed onto paper or the like and dried in an oven at 70° C. for 10 minutes to flash off the solvent. The dried coated polyurethane is tested for elutable silver by placing a section of the coated paper under an ultraviolet lamp, adding a drop of water to a section of the paper and exposing the drop of water to the UV light for 30 to 60 minutes. It can be observed that the drop of water eventually turns gray however, the time to turn the drop of water gray is significantly longer than the silver sulfonated polyurethane described in Example 1. This example suggests that the polyurethane is not as hydrophilic as Example 1 and does not as readily release the silver ion.

Coated sections of paper were then tested for antimicrobial activity by NAMSA using the Dow 923 "Shake-flask" test which involves shaking the sample in a flask with *staphylococcus aureus* bacteria for 1 hour and then for 24 hours and measuring the amount of bacteria killed. Results indicate that at one hour, 96.56%, or essentially most of the bacteria were killed. The results at 24 hours indicate that 99.94% of the bacterial charge was killed confirming that this formulation is bactericidal but not as effective as Example 1.

EXAMPLE 3

Control samples consisting of the same paper with the polyurethane binder alone, i.e., without the silver, killed 45.95% of the bacteria in one hour and 99.94% in 24 hours. An additional control sample of just the bottle alone showed a 38.89% reduction in bacteria at 24 hours. These controls indicate that the bottle as well as the paper with polyurethane coating are both somewhat bactericidal but not as much as the silver-treated samples of Examples 1 and 2.

CONCLUSIONS REGARDING EXAMPLES 1–3

Any polymer can be used as the binder or carrier for the silver ion, such as polyurethane, polyolefin, silicone rubber, natural rubber, polyvinyl chloride, polyamide, polyester, cellulose, acetate, etc. as long as the polymer can be dissolved in a solvent or dispersed as a latex in a solvent. However, it is preferred that the polymer be somewhat hydrophilic to provide an aqueous medium for the silver ion to migrate towards the microbe. Preferred hydrophilic polymers include hydrophilic polyurethane, hydrogels such as poly(2-hydroxyethyl methacrylate), polyacrylamide, polyvinylpyrrolidone, etc. More preferred is a hydrophilic polyurethane that can bind a metal cation such as silver. The sulfonated polyurethane described in the above examples are such polyurethanes. Sulfonated hydrogels may also function in this capacity.

Metal ions other than silver (e.g. zinc) can be used as the antimicrobial agent. Silver is preferred because it is the most efficient of the metal ions for antimicrobial purposes.

In the above examples, it is preferable that polymer solutions of 0.5% to 45% be used. Polymer solutions with higher solids content are difficult to dissolve and difficult to mix. 5% to 15% solids is the most preferred range.

Although the solvent system of 20%/80% DMA/THF was used in Example 1 and 2, alternate solvents can be used to dissolve polyurethane such as m-pyrol, dimethylformamide, dimethylacetamide, dimethyl sulfonamide, mixtures of the above, mixtures of the above with swelling solvents such as diethyl ether, tetrahydrofuran, xylene, toluene etc. and the like. DMA/THF is preferred due to the ease of handling.

The concentration of acetic anhydride and sulfuric acid is equimolar. These chemicals combine in situ to sulfonate the polyurethane. The amount of sulfonation is controlled by the ratio of acetic anhydride/sulfuric acid to polymer. A suitable range of acetic anhydride/sulfuric acid:polyurethane, in mL/mL:g is 21/12.5:1 to 21/12.5:100. It was found empirically that about 21 ml of acetic anhydride and 12.5 ml of concentrated sulfuric acid to a solution with 10 g polyurethane provides a good balance of hydrophilicity to tensile strength. Too many sulfate groups on the polyurethane lower the tensile strength. Too few do not readily produce a hydrophilic polyurethane.

The sulfonation concentration of 2% of solids content was described in Example 1. Other samples made at 0.5%, 10% and 20% also functioned as desired. However high loading of silver is unnecessarily expensive. Nevertheless, too low a loading may deplete the reservoir of available silver too quickly (i.e., in days rather than months or years). A concentration of 2% was selected as a rational intermediate concentration.

The concentration of silver sulfadiazine in Example 2 was 2% in respect to solids. Acceptable ranges are 0.1% to 20% for the same reasons as discussed in the previous paragraph.

The solutions described above can be used to coat virtually any kind of paper. According to methods of the invention, it is expected that the antimicrobial solutions be used to coat paper used in sending mail such as envelopes and note paper. It is also expected that the antimicrobial solutions be used to coat financial instruments and paper currency which might be used by a terrorist to spread disease.

EXAMPLE 4

The antimicrobial solution of Example 1 is prepared and is squeegeed onto both sides of a U.S. one dollar bill. The dollar bill is dried in an oven at 70° C. for 10 minutes to flash off the solvent. The coated dried dollar bill exhibits the same antimicrobial activity as the paper in Example 1.

Paper coated with the antimicrobial solution of the invention can be imprinted using offset printing, silkscreen printing, letterpress, rotogravure, flexible printing, liquid lamination, or coating.

The antimicrobial solutions may be applied to other products as described or by spraying, dipping, etc. According to the methods of the invention, it is also expected that the antimicrobial solution be applied to medical products such as surgical tools and implantable medical devices. If the medical device is polymeric, the antimicrobial agent can be applied as described in Example 4.

EXAMPLE 5

A polymeric medical device such as a catheter is sulfonated and rendered antimicrobial as follows.

A sulfonating solution is prepared with 93.3 ml 2-propanol, 4.2 ml acetic anhydride and 2.5 ml of concentrated sulfuric acid (added slowly). The solution is heated from room temperature to as high as the boiling point of the solvent; 60° C.±3° C., preferably with stirring. This sulfonating solution can be prepared in solvents other than 2-propanol, such as water, hexane, heptane, alcohols, etc., as long as the acetic anhydride and sulfuric acid are capable of dissolving in the solvent and the solvent is capable of wetting the polymer. 2-propanol is preferred for this reason. The ratio of 4.2 ml of acetic anhydride to 2.5 ml of sulfuric acid is selected so as to be a 1:1 molar ratio with the concentrated sulfuric acid.

The polymeric medical device is immersed in the above solution for 0.1 second to as long as 30 minutes; 10 seconds to 10 minutes is preferred. The device is removed and rinsed in deionized water for 1 to 30 minutes, 1 to 2 minutes with agitation is preferred. Ammonium hydroxide can be added to the deionized water to bring the pH back to neutral if necessary. The sulfonated polymeric device can be dried and stored, or it can immediately be rendered antimicrobial in the following manner.

A 2% silver nitrate solution is prepared by adding 2 g of silver nitrate to 100 ml of 2-propanol. The sulfonated polymeric device is immersed in this solution for 1 to 300 minutes; 30 minutes is preferred. The device is then rinsed in water and dried. The silver ion ionically bonds to the sulfate groups on the polymer. The concentration of silver nitrate can be between 0.01% and 20%. For economic reasons 0.1% to 2% is used. The solvent for the silver nitrate is 2-propanol, however any solvent capable of dissolving silver nitrate and wetting the polymer can be used such as water, alcohols, etc.

An alternative method of producing a medical device according to the invention is demonstrated in Example 6.

EXAMPLE 6

A polymer solution is made by dissolving 10 g of an aromatic polyether urethane such as Dow Chemical's Pellethane® 2363 75D in 90 g dimethyl acetamide (DMA) at 70° C. with mixing for 3 hours.

The polyurethane is sulfonated and rendered hydrophilic by adding 21 ml of acetic anhydride and 12.5 ml of concentrated sulfuric acid to the polyurethane solution while it is being vigorously mixed. After the exothermic reaction subsides, the hydrophilic urethane is poured into a blender filled with water where the polyurethane is precipitated and chopped into small particles under agitation. The particulate slurry is poured through a wire sieve to remove the particles and rinsed repeatedly with water until the pH of the solution is between 4 and 8. The precipitated sulfonated polyurethane is then dried for 3 hours in an oven at 70° C.

The dried sulfonated polyurethane (10 g) is then redissolved in 90 g DMA and then reacted with silver nitrate by adding 0.2 g (2% by weight of polymer) of silver nitrate to the sulfonated polyurethane solution. The solution is again precipitated and chopped into particles by pouring the solution into a blender containing water. The particles are rinsed repeated in water and then dried in a vacuum oven overnight at 70° C.

The dried particles containing silver, bound to sulfate groups on a polyurethane, are thermoplastic and can readily be extruded, injection molded, compression molded, or solvent cast into medical devices, and the like, using standard plastic processing equipment well known to people versed in the art of processing plastics.

In this manner, for example, catheters containing silver ion can be extruded directly without going through a second procedure. Preferred materials for the catheter (or other polymeric medical device) include polyurethane, polyolefin, polyester, polyamide (Nylon and the like), polyimide and any other polymer capable of being sulfonated with the above reactants. The presently preferred polymer is polyurethane.

Polymeric medical devices that can benefit from antimicrobial activity include catheters, ports, scopes (endoscopes and the like) implantable devices in general, such as stents, vascular grafts, hip and knee acetabular joints, pacer lead insulators, spinal disks, sutures, stent grafts, etc.

As mentioned above, non-polymeric medical devices can be treated using the polymeric solutions described in Examples 1, 2 and 6.

EXAMPLE 7

Dried sulfonated polyurethane containing silver ion made according to Example 6 is dissolved in tetrahydrofuran at 5% solids content and squeegee-coated onto paper and flashed dried, thereby rendering the surface of the paper antimicrobial. Coatings made in this manner are similar to those described in Example 1. However, the dried polymer has a longer shelf life and is less expensive to inventory as compared to lacquers, and is therefore generally preferred.

There have been described and illustrated herein antimicrobial agents, products incorporating said agents and methods of making the antimicrobial agents and products incorporating them. While particular embodiments of the invention have been described, it is not intended that the invention be limited thereto, as it is intended that the invention be as broad in scope as the art will allow and that the specification be read likewise. It will therefore be appreciated by those skilled in the art that yet other modifications could be made to the provided invention without deviating from its spirit and scope as so claimed.

What is claimed is:

1. An antimicrobial agent comprising:
   an oligodynamic metal ion reacted with an acidic group counter-ion of a hydrophilic polymer having said counter-ion bound to it, said hydrophilic polymer controlling a sustained release of the metal ion, and said hydrophilic polymer including polyurethane.

2. An antimicrobial agent according to claim 1, wherein:
   said oligodynamic metal ion is selected from the group consisting of Ag, Au, Pt, Pd, Ir, Cu, Sn, Sb, Bi and Zn.

3. An antimicrobial agent according to claim 1, wherein:
   said oligodynamic metal ion is Ag+.

4. An antimicrobial agent according to claim 1, wherein:
   said hydrophilic polymer is sulfonated polyurethane.

5. An antimicrobial agent according to claim 1, wherein:
   said oligodynamic metal ion is Ag+, and
   said hydrophilic polymer is sulfonated polyurethane.

6. An antimicrobial agent according to claim 1, wherein:
   said acidic group counter-ion is selected from a group consisting of a carboxylic acid, a sulfonate, a phosphate, and a nitrate.

7. An antimicrobial agent according to claim 6, wherein:
   said hydrophilic polymer includes a polymer with a sulfonate counter-ion.

8. An antimicrobial agent according to claim 7, wherein:
   said oligodynamic metal ion is Ag+.

9. An antimicrobial agent according to claim 6, wherein:
   said oligodynamic metal ion is Ag+.

10. An antimicrobial agent comprising:
    an oligodynamic metal ion reacted with an acidic group counter-ion of a hydrophilic bulk polymer having said counter-ion bound to it, said hydrophilic bulk polymer controlling a sustained release of the metal ion, and said hydrophilic bulk polymer including polyurethane.

11. An antimicrobial agent according to claim 10, wherein:
    said oligodynamic metal ion is selected from the group consisting of Ag, Au, Pt, Pd, Ir, Cu, Sn, Sb, Bi and Zn.

12. An antimicrobial agent according to claim 10, wherein:
    said oligodynamic metal ion is Ag+.

13. An antimicrobial agent according to claim 10, wherein:
    said hydrophilic bulk polymer is sulfonated polyurethane.

14. An antimicrobial agent according to claim 10, wherein:
    said oligodynamic metal ion is Ag+, and
    said hydrophilic bulk polymer is sulfonated polyurethane.

15. An antimicrobial agent according to claim 10, wherein:
    said acidic group counter-ion is selected from a group consisting of a carboxylic acid, a sulfonate, a phosphate, and a nitrate.

16. An antimicrobial agent according to claim 15, wherein:
    said hydrophilic polymer includes a polymer with a sulfonate counter-ion.

17. An antimicrobial agent according to claim 16, wherein:
    said oligodynamic metal ion is Ag+.

18. An antimicrobial agent according to claim 15, wherein:
    said oligodynamic metal ion is Ag+.

19. An antimicrobial agent comprising:
    an oligodynamic metal ion reacted with an acidic group counter-ion of a hydrophilic homo-polymer having said counter-ion bound to it, said hydrophilic homopolymer controlling a sustained release of the metal ion, and said hydrophilic homopolymer including polyurethane.

20. An antimicrobial agent according to claim 19, wherein:

said oligodynamic metal ion is selected from the group consisting of Ag, Au, Pt, Pd, Ir, Cu, Sn, Sb, Bi and Zn.

21. An antimicrobial agent according to claim 19, wherein:

said oligodynamic metal ion is Ag+.

22. An anticmicrobial agent according to claim 19, wherein:

said hydrophilic homo polymer is sulfonated polyurethane.

23. An antimicrobial agent according to claim 19, wherein:

said oligodynamic metal ion is Ag+, and said hydrophilic homopolymer is sulfonated polyurethane.

24. An antimicrobial agent according to claim 19, wherein:

said acidic group counter-ion is selected from a group consisting of a carboxylic acid, a sulfonate, a phosphate, and a nitrate.

25. An antimicrobial agent according to claim 24, wherein:

said hydrophilic homopolymer includes a polymer with a sulfonate counter-ion.

26. An antimicrobial agent according to claim 25, wherein:

said oligodynamic metal ion is Ag+.

27. An antimicrobial agent according to claim 24, wherein:

said oligodynamic metal ion is Ag+.

* * * * *